(12) United States Patent
Sun et al.

(10) Patent No.: US 7,169,782 B2
(45) Date of Patent: Jan. 30, 2007

(54) ARYL SUBSTITUTED THIAZOLIDINONES AND THE USE THEREOF

(75) Inventors: Qun Sun, Princeton, NJ (US); Donald J. Kyle, Newtown, PA (US); Parviz Gharagozloo, Pennington, NJ (US); Ji Yang, Princeton Junction, NJ (US)

(73) Assignee: Euro-Celtique S.A., Luxembourg (LU)

( * ) Notice: Subject to any disclaimer, the term of this patent is extended or adjusted under 35 U.S.C. 154(b) by 0 days.

(21) Appl. No.: 10/195,530

(22) Filed: Jul. 16, 2002

(65) Prior Publication Data
US 2003/0109521 A1 Jun. 12, 2003

Related U.S. Application Data

(60) Provisional application No. 60/305,099, filed on Jul. 16, 2001.

(51) Int. Cl.
- C07D 277/14 (2006.01)
- C07D 417/06 (2006.01)
- A61K 31/426 (2006.01)
- A61K 31/4439 (2006.01)

(52) U.S. Cl. .............. 514/236.8; 514/326; 514/342; 514/369; 544/133; 546/209; 546/269.7; 548/186

(58) Field of Classification Search ........ 548/186; 514/369, 236.8, 326, 342; 544/133; 546/209, 546/269.7
See application file for complete search history.

(56) References Cited

U.S. PATENT DOCUMENTS

| | | | |
|---|---|---|---|
| 3,309,377 A * | 3/1967 | Surrey | ............... 548/186 |
| 3,377,355 A | 4/1968 | Surrrey | |
| 4,933,453 A | 6/1990 | Hrib et al. | |
| 5,061,720 A | 10/1991 | Walsh et al. | |
| 5,229,388 A | 7/1993 | Hrib et al. | |
| 6,335,354 B2 | 1/2002 | Hogenkamp | |
| 6,414,011 B1 | 7/2002 | Hogenkamp et al. | |
| 2002/0006947 A1 | 1/2002 | Hogenkamp et al. | |
| 2002/0040025 A1 | 4/2002 | Hogenkamp et al. | |
| 2003/0055088 A1 | 3/2003 | Shao et al. | |

FOREIGN PATENT DOCUMENTS

| | | |
|---|---|---|
| DE | 22 59 222 | 6/1973 |
| EP | 0 292 305 A1 | 11/1988 |
| EP | 0 524 595 A1 | 1/1993 |
| EP | 0 699 675 A2 | 3/1996 |
| EP | 0 705 816 A1 | 4/1996 |
| GB | 1 409 898 | 10/1975 |
| WO | WO 99/62891 A1 | 12/1999 |
| WO | WO 00/57877 A1 | 10/2000 |
| WO | WO 00/63197 A1 | 10/2000 |

OTHER PUBLICATIONS

Andres Bloorganic an Medicinal Chemistry Letters 10 (2000) 715-7.*
Bensimon, G., et al., "A Controlled Trial of Riluzole in Amyotrophic Lateral Sclerosis," *New Engl. J. Med.* 330:585-591, Massachusetts Medical Society (1994).
Brown, C.M., et al., "Neuroprotective properties of lifarizine compared with those of other agents in a mouse model of focal cerebral ischaemia," *British J. Pharmacol.* 115:1425-1432, Stockton Press (1995).
Buchan, A.M., et al., "AMPA Antagonists: Do They Hold More Promise for Clinical Stroke Trials Than NMDA Antagonists?" *Stroke Suppl. I* 24:I-148-I-152, American Heart Association (1993).
Catterall, W.A., "Neurotoxins that Act on Voltage-Sensitive Sodium Channels in Excitable Membranes," *Ann. Rev. Pharmacol. Toxicol.* 20:15-43, Annual Reviews, Inc. (1980).
Catterall, W.A., "Common modes of drug action on $Na^+$ channels: local anesthetics, antiarrhythmics and anticonvulsants," *Trends Pharmacol. Sci.* 8:57-65, Elsevier Science B.V. (1987).
Catterall, W.A., "Structure and Function of Voltage-Sensitive Ion Channels," *Science* 242:50-61, American Association for the Advancement of Science (1988).

(Continued)

*Primary Examiner*—Fiona T. Powers
(74) *Attorney, Agent, or Firm*—Sterne, Kessler, Goldstein & Fox P.L.L.C.

(57) ABSTRACT

This invention relates aryl substituted thiazolidinones of Formula I:

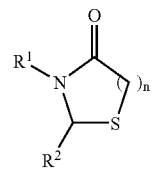

or a pharmaceutically acceptable salt, or solvate thereof, wherein $R_1$ and $R_2$, are defined in the specification. The invention is also directed to the use of compounds of Formula I for the treatment of neuronal damage following global and focal ischemia, for the treatment or prevention of neurodegenerative conditions such as amyotrophic lateral sclerosis (ALS), and for the treatment, prevention or amelioration of both acute or chronic pain, as antitinnitus agents, as anticonvulsants, and as antimanic depressants, as local anesthetics, as antiarrhythmics and for the treatment or prevention of diabetic neuropathy.

39 Claims, No Drawings

OTHER PUBLICATIONS

Creveling, C.R., et al., "Batrachotoxin-Induced Depolarization and [$^3$H] Batrachotoxinin-A 20α-Benzoate Binding in a Vesicular Preparation from Guinea Pig Cerebral Cortex," *Mol. Pharmacol.* 23:350-358, The American Society for Pharmacology and Experimental Therapeutics (1983).

Denicoff, K.D., et al., "Efficacy of Carbamazepine Compared With Other Agents: A Clinical Practice Survey," *J. Clin. Psychiatry* 55:70-76, Physicians Postgraduate Press (1994).

Donaldson, I., "Tegretol: A double blind trial in tinnitus," *J. Laryngol. Otol.* 95:947-951, Headley Brothers (1981).

Graham, S.H., et al., "Neuroprotective Effects of a Use-Dependent Blocker of Voltage-Dependent Sodium Channels, BW619C89, in Rat Middle Cerebral Artery Occlusion," *J. Pharmacol. Exp. Ther.* 269:854-859, Williams & Wilkins (1994).

Graham, S.H., et al., "A Dose-Response Study of Neuroprotection Using the AMPA Antagonist NBQX in Rat Focal Cerebral Ischemia," *J. Pharmacol. Exp. Ther.* 276:1-4, Williams & Wilkins (1996).

Hunskaar, S., et al., "Formalin test in mice, a useful technique for evaluating mild analgesics," *J. Neurosci. Methods* 14:69-76, Elsevier Science B.V. (1985).

Iwasaki, Y., et al., "CNQX prevents spinal motor neuron death following sciatic nerve transection in newborn rats," *J. Neurological Sci.* 134:21-25, Elsevier Science B.V. (1995).

Leff, P., and Dougall, I.G., "Further concerns over Cheng-Prusoff analysis," *Trends Pharmacol. Sci.* 14:110-112, Elsevier Science Publishers Ltd. (1993).

Majumdar, B., et al., "An electrocochleographic study of the effects of lignocaine on patients with tinnitus," *Clin. Otolaryngol.* 8:175-180, Blackwell Scientific Publications (1983).

Møller, A.R., "Similarities Between Chronic Pain and Tinnitus," *Am. J. Otol.* 18:577-585, Lippincott-Raven (1997).

Ohizumi, Y., et al., "Specific Inhibition of [$^3$H] Saxitoxin Binding to Skeletal Muscle Sodium Channels by Geographutoxin II, a Polypeptide Channel Blocker," *J. Biol. Chem.* 261:6149-6152, The American Society of Biological Chemists, Inc. (1986).

Sheardown, M.J., et al., "AMPA, but not NMDA, receptor antagonism is neuroprotective in gerbil global ischaemia, even when delayed 24 h," *Eur. J. Pharmacol.* 236:347-353, Elsevier Science B.V. (1993).

Simpson, J.J., and Davies, W.E., "Recent advances in the pharmacological treatment of tinnitus," *Trends Pharmacol. Sci.* 20:12-18, Elsevier Science London (1999).

Stys, P.K., et al., "Ionic Mechanisms of Anoxic Injury in Mammalian CNS White Matter: Role of Na$^+$ Channels and Na$^+$—Ca2$^+$ Exchanger," *J. Neurosci.* 12:430-439, Society for Neuroscience (1992).

Taylor, C.P., and Meldrum, B.S., "Na$^+$ channels as targets for neuroprotective drugs," *Trends Pharmacol. Sci.* 16:309-316, Elsevier Science Ltd. (1995).

Tonndorf, J., "The analogy between tinnitus and pain: A suggestion for a physiological basis of chronic tinnitus," *Hear. Res.* 28:271-275, Elsevier Science B.V. (1987).

Woodward, R.M., et al., "Effects of Steroids on γ-Aminobutyric Acid Receptors Expressed in *Xenopus* Oocytes by Poly(A)$^+$ RNA from Mammalian Brain and Retina," *Mol. Pharmacol.* 41:89-103, Williams and Wilkins (1992).

Wrathall, J.R., et al., "Amelioration of Functional Deficits from Spinal Cord Trauma with Systemically Administered NBQX, an Antagonist of Non-N-methyl-D-aspartate receptors," *Exp. Neurol.* 137:119-126, Academic Press, Inc. (1996).

Koga, T., et al., "The protective effects of CP-060S on ischaemia- and reperfusion-induced arrhythmias in anaesthetized rats," *Br. J. Pharmacol.* 123:1409-1417, Stockton Press (1998).

International Search Report for International Patent Application No. PCT/US02/22367, mailed Oct. 9, 2002.

Andres, C.J., et al., "4-Thiazolidinones: Novel Inhibitors of the Bacterial Enzyme MurB," *Bioorg. Med. Chem. Lett.* 10:715-717, Pergamon Press (2000).

Bartoszyk, G.D., et al., "Ralitoline: a thiazolidinone," *Curr. Probl. Epilepsy* 4:309-311, John Libbey (1986).

Bhat, A.R., et al., "Synthesis and Biological Activity of Some 3-(1,3,4-oxadiazol-2-yl)-2-aryl-4-thiazolidinones," *Indian Drugs* 21:129-134, Indian Drug Manufacturers' Association (1984).

Capan, G., et al., "Synthesis and Anticonvulsant Activity of New 3-[(2-furyl)carbonyl]amino-4-thiazolidinone and 2-[(2-furyl)carbonyl]hydrazono-4-thiazoline Derivatives," *Il Farmaco* 51:729-732, Societa Chimica Italiana (1996).

Cesur, N., et al., "New Acylthiosemicarbazides, Thiazolidinones, and 1,3,4-Oxadiazoles as Possible Anticonvulsants," *Arch. Pharm.* (Weinheim, Ger.) 325:623-624, VCH Verlagsgesellschaft mbH (1992).

El-Meligie, S., "Synthesis of Certain Thiazolidinone Derivatives as Possible Anticonvulsants," *Bull. Fac. Pharm. Cairo Univ.* 28:35-37, Cairo University (1990).

El-Shafei, A.K., and Hassan, K.M., "Synthesis of Some New N-Oxidopyridylthiazolidin-4-ones," *Curr. Sci.* 52:633-635, Current Science Association (1983).

Ergenc, N., and Capan, G., "Synthesis and Anticonvulsant Activity of New 4-Thiazolidone and 4-Thiazoline Derivatives," *Il Farmaco* 49:449-451, Societa Chimica Italiana (1994).

Fischer, W., et al., "Anticonvulsant and sodium channel blocking effects of ralitoline in different screening models," *Naunyn-Schmiedeberg's Arch. Pharmacol.* 346:442-452, Springer-Verlag (1992).

Gahane, D.R., et al., "Mannich Reaction Products of 5-Arylidene-2-phenylimino-4-thiazolidinones as Anticonvulsants," *Indian J. Pharm. Sci.* 60:275-279, Indian Pharmaceutical Association (1998).

Gaikwad, N.J., and Agrawal, S.B., "Substituted 4-Thiazolidinones as Anticonulsants VII," *Indian Drugs* 34:542-543, Indian Drug Manufacturers' Association (1997).

Gaikwad, N.J., and Tirpude, R.N., "Substituted 4-Thiazolidinones as Anticonvulsants V," *Indian Drugs* 31:593-594, Indian Drug Manufacturers' Association (1994).

Gaikwad, N.J., and Shah, K., "Substituted 4-Thiazolidinones as Anticonulsants IV," *Indian Drugs* 26:341-342, Indian Drug Manufacturers' Association (1989).

Gaikwad, N.J., et al., "Substituted 4-Thiazolidinones as Anticonvulsants. III," *Indian Drugs* 24:288-289, Indian Drug Manufacturers' Association (1987).

Gaikwad, N.J., et al., "Substituted 4-Thiazolidinones as Anticonvulsants," *Indian Drugs* 23:384-385, Indian Drug Manufacturers' Association (1986).

Gupta, R.C., et al., "Biologically Active Thiazolidinone," *J. Indian Chem. Soc.* 55:832-834, The Indian Chemical Society (1978).

Husain, M.I., and Amir, M., "Synthesis of some new 2-arylimino-3-[p-(3,4,5-trimethoxybenzamido)benzoylamino]-thiazolid-4-ones as possible anticonvulsant agents," *Acta Pharm. Jugosl.* 35:167-173, Federation of Yugoslav Pharmaceutical Association (1985).

Loscher, W., et al., "Ralitoline: A Reevaluation of Anticonvulsant Profile and Determination of 'Active' Plasma Concentrations in Comparison with Prototype Antiepileptic Drugs in Mice," *Epilepsia* 32:560-568, Raven Press, Ltd. (1991).

Mishra, S., et al., "Synthesis of 5-arylidene-2-aryl-3-(phenothiazino/benzotriazoloacetamidyl)-1,3-thiazolidine-4-ones as antiinflammatory, anticonvulsant, analgesic and antimicrobial agents," *Indian. J. Chem.* 36B:826-830, Council Of Scientific And Industrial Research (1997).

Omar, A., et al., "Some Novel Theophylline Thiosemicarbazide and Thiazolidinone Derivatives as Potential Anticancer and Anticonvulsant Agents," *Pharmazie* 34:110-111, VEB Verlag Volk und Gesundheit (1979).

Parmar, S.S., et al., "Substituted Thiazolidones and Their Selective Inhibition of Nicotinamide-Adenine Dinucleotide Dependent Oxidations," *J. Med. Chem.* 15:99-101, American Chemical Society (1972).

Ragab, F.A., et al., "Synthesis and anticonvulsant activity of new thiazolidinone and thioxoimidazolidinone derivatives derived from furochromones," *Pharmazie* 52:926-929, Govi-Verlag Pharmazeutischer Verlag GmbH (1997).

Ragab, F.A., et al., "Synthesis, Anticonvulsant and Antimcrobial Activities of Certain New Furochromones," *Egypt. J. Phar. Sci.* 34:387-400, National Information and Documentation Center (1993).

Ragab, F.A., and Sief-El-Nasr, M., "Synthesis and Anticonvulsant Activity of Some Ureido Thiazolidinone and Thiohydantoin Derivatives of Furochromones," *Bull. Fac. Pharm. 30:*209-213, Cairo University (1992).

Singh, V.P., et al., "Thiazolidinones: A Review," *Asian J. Chem. Rev. 3:*12-21, Chemic Publishing Co. (1992).

Srivastava, S.K., et al., "Synthesis of 5-arylidene-2-aryl-3-(2-chlorophenothiazinoacetamidyl)-1,3-thiazolidin-4-ones as antifungal and anticonvulsant agents," *J. Indian Chem. Soc. 77:*104-105, The Indian Chemical Society (Feb. 2000).

Ulusoy, N., et al., "Synthesis and Anticonvulsant Activity of Some New Arylidenehydrazides and 4-Thiazolidinones," *Monatsh. Chem. 127:*1197-1202, Springer-Verlag (1996).

* cited by examiner

US 7,169,782 B2

ARYL SUBSTITUTED THIAZOLIDINONES AND THE USE THEREOF

This application claims the priority benefit under 35 U.S.C. § 119(e) of U.S. Provisional Application No. 60/305,099, filed Jul. 16, 2001, the entirety of which is incorporated by reference herein.

BACKGROUND OF THE INVENTION

1. Field of the Invention

This invention is in the field of medicinal chemistry. In particular, the invention relates to novel aryl substituted thiazolidinones, and the discovery that these compounds are blockers of sodium ($Na^+$) channels.

2. Related Art

Several classes of therapeutically useful drugs, including local anesthetics such as lidocaine and bupivacaine, antiarrhythmics such as propafenone and amioclarone, and anticonvulsants such as lamotrigine, phenytoin and carbamazepine, have been shown to share a common mechanism of action by blocking or modulating $Na^+$ channel activity (Catterall, W. A., *Trends Pharmacol. Sci.* 8:57–65 (1987)). Each of these agents is believed to act by interfering with the rapid influx of $Na^+$ ions.

Recently, other $Na^+$ channel blockers such as BW619C89 and lifarizine have been shown to be neuroprotective in animal models of global and focal ischemia and are presently in clinical trials (Graham et al., *J. Pharmacol. Exp. Ther.* 269:854–859 (1994); Brown et al., *British J. Pharmacol.* 115:1425–1432 (1995)).

The neuroprotective activity of $Na^+$ channel blockers is due to their effectiveness in decreasing extracellular glutamate concentration during ischemia by inhibiting the release of this excitotoxic amino acid neurotransmitter. Studies have shown that unlike glutamate receptor antagonists, $Na^+$ channel blockers prevent hypoxic damage to mammalian white matter (Stys et al., *J. Neurosci.* 12:430–439 (1992)). Thus, they may offer advantages for treating certain types of strokes or neuronal trauma where damage to white matter tracts is prominent.

Another example of clinical use of a $Na^+$ channel blocker is riluzole. This drug has been shown to prolong survival in a subset of patients with ALS (Bensimm et al., *New Engl. J. Med.* 330:585–591 (1994)) and has subsequently been approved by the FDA for the treatment of ALS. In addition to the above-mentioned clinical uses, carbamazepine, lidocaine and phenytoin are occasionally used to treat neuropathic pain, such as from trigeminal neurologia, diabetic neuropathy and other forms of nerve damage (Taylor and Meldrum, *Trends Pharmacol. Sci.* 16:309–316 (1995)), and carbamazepine and lamotrigine have been used for the treatment of manic depression (Denicott et al., *J. Clin. Psychiatry* 55:70–76 (1994)). Furthermore, based on a number of similarities between chronic pain and tinnitus, (Moller, A. R. *Am. J. Otol.* 18:577–585 (1997); Tonndorf, *J. Hear. Res.* 28:271–275 (1987)) it has been proposed that tinnitus should be viewed as a form of chronic pain sensation (Simpson, J. J. and Davies, E. W. *Tips.* 20:12–18 (1999)). Indeed, lignocaine and carbamazepine have been shown to be efficacious in treating tinnitus (Majumdar, B. et al. *Clin. Otolaryngol.* 8:175–180 (1983); Donaldson, I. *Laryngol. Otol.* 95:947–951 (1981)).

It has been established that there are at least five to six sites on the voltage-sensitive $Na^+$ channels which bind neurotoxins specifically (Catterall, W. A., *Science* 242:50–61 (1988)). Studies have further revealed that therapeutic antiarrhythmics, anticonvulsants and local anesthetics whose actions are mediated by $Na^+$ channels, exert their action by interacting with the intracellular side of the $Na^+$ channel and allosterically inhibiting interaction with neurotoxin receptor site 2 (Catterall, W. A., *Ann. Rev. Pharmacol. Toxicol.* 10:15–43 (1980)).

A need exist in the art for novel compounds that are potent blockers of sodium channels, and are therefore useful for treating a variety of central nervous system conditions, including pain.

SUMMARY OF THE INVENTION

The present invention is related to the discovery that aryl substituted thiazolidinones represented by Formula I act as blockers of sodium ($Na^+$) channels.

Another aspect of the present invention is directed to the use of novel compounds of Formula I as blockers of sodium channels.

The invention is also related with treating a disorder responsive to the blockade of sodium channels in a mammal suffering from excess activity of said channels by administering an effective amount of a compound of Formula I as described herein.

One aspect of the present invention is directed to the novel aryl substituted thiazolidinones of Formula I.

A further aspect of the present invention is to provide a method for treating, preventing or ameliorating neuronal loss following global and focal ischemia; treating, preventing or ameliorating pain including acute and chronic pain, and neuropathic pain; treating, preventing or ameliorating convulsion and neurodegenerative conditions; treating, preventing or ameliorating manic depression; using as local anesthetics and anti-arrhythmics, and treating tinnitus by administering a compound of Formula I to a mammal in need of such treatment or use.

Also, an aspect of the present invention is to provide a pharmaceutical composition useful for treating disorders responsive to the blockade of sodium ion channels, containing an effective amount of a compound of Formula I in a mixture with one or more pharmaceutically acceptable carriers or diluents.

Additional embodiments and advantages of the invention will be set forth in part in the description that follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

The present invention arises out of the discovery that aryl substituted thiazolidinones of Formula I are anticonvulsants and act as blockers of $Na^+$ channels. In view of this discovery compounds of Formula I are useful for treating disorders responsive to the blockade of sodium ion channels.

Novel compounds of the present invention are aryl substituted thiazolidinones represented by Formula I:

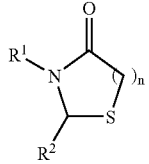

or a pharmaceutically acceptable salt, or solvate thereof, wherein:

n is an integer from 1 to 2;

R₁ is selected from the group consisting of:

(i)

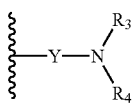

where Y is alkylene, and

R₃ and R₄ are the same or different and are selected from hydrogen, alkyl, or aryl, or R₃ and R₄ together form an alkylene chain having 4 to 5 carbon atoms optionally interrupted by a nitrogen or oxygen;

(ii) pyridylalkyl; and (iii) piperidin-4-ylalkyl, optionally substituted by alkyl, aryl or aralkyl; and R₂ is selected from the group consisting of:

(i) optionally substituted phenoxyphenyl;

(ii) optionally substituted phenoxythiophenyl;

(iii) optionally substituted benzyloxyphenyl;

(iv) optionally substituted benzylthiophenyl;

(v)

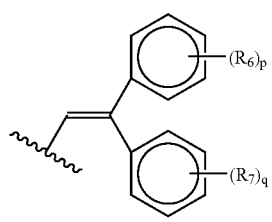

wherein R₆ and R₇ are independently hydrogen, alkyl, alkoxy, halo or haloalkyl; and p and q are independently integers from 0 to 4;

(vi)

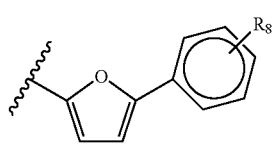

wherein R₈ is hydrogen, halogen or alkyl;

(vii)

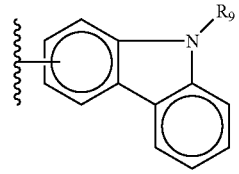

wherein R₉ is hydrogen or alkyl; and (viii) naphthalenyl.

Preferred compounds are those of Formula I wherein R₁ is

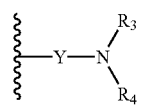

and Y is ethylene or propylene.

Preferred compounds are additionally those of Formula I wherein R₁ is

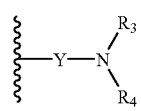

where R₃ and R₄ together form an alkylene chain having 4 to 5 carbon atoms;

Y is an optionally substituted $C_{1-6}$ alkylene chain; and

R₂ is phenoxyphenyl or benzyloxyphenyl, wherein the phenoxy moiety is optionally substituted with alkyl, halogen or haloalkyl.

Preferred compounds also are those of Formula I wherein R₁ is pyridyl($C_{1-4}$)alkyl.

Preferred compounds are those of Formula I wherein R₁ is

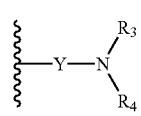

where R₃ and R₄ are independently hydrogen, alkyl or alkenylaryl, Y is an optionally substituted $C_{1-4}$ alkylene chain; and R₂ is phenoxyphenyl or benzyloxyphenyl, wherein the phenoxy moiety is optionally substituted with alkyl, halogen or haloalkyl.

Preferred compounds also are those of Formula I wherein R₁ is

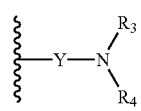

where R₃ and R₄ together form an alkylene chain having 4 to 5 carbon atoms;

Y is an optionally substituted $C_{1-6}$ alkylene chain; and $R_2$ is

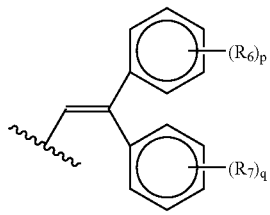

Preferred compounds also are those of Formula I wherein $R_1$ is

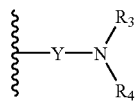

where $R_3$ and $R_4$ are independently hydrogen, alkyl or alkylenylaryl, Y is an optionally substituted $C_{1-4}$ alkylene chain; and
$R_2$ is

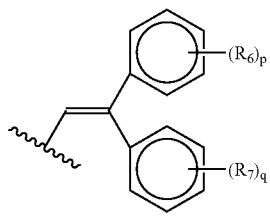

Additionally, preferred compounds also are those of Formula I wherein
$R_1$ is

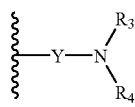

where $R_3$ and $R_4$ together form an alkylene chain having 4 to 5 carbon atoms;
Y is an optionally substituted $C_{1-6}$ alkylene chain; and
$R_2$ is

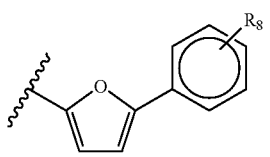

Additionally, preferred compounds also are those of Formula I wherein
$R_1$ is

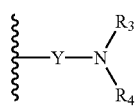

where $R_3$ and $R_4$ together form an alkylene chain having 4 to 5 carbon atoms;
Y is an optionally substituted $C_{1-6}$ alkylene chain; and $R_2$ is

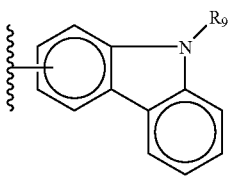

Preferred compounds also are those of Formula I wherein $R_1$ is

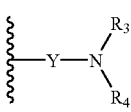

where $R_3$ and $R_4$ together form an alkylene chain having 4 to 5 carbon atoms;
Y is an optionally substituted $C_{1-6}$ alkylene chain; and $R_2$ is naphthalene.

For purposes of the present invention, the term "alkylene" has the meaning —$(CH_2)_m$—, where m is an integer of from 1–6, preferably 2–4. Suitable alkylene chains include but are not limited to methylene, ethylene, propylene, butylene, pentylene and hexylene. The alkylene chain may also be optionally substituted.

The term "alkyl" means a linear or branched $C_{1-10}$ carbon chain, preferably a $C_{1-6}$ carbon chain. Suitable alkyl groups include, but are not limited to, methyl, ethyl, propyl, isopropyl, butyl, isobutyl, sec-butyl, tert-butyl, 3-pentyl, hexyl and octyl groups.

The term "optionally substituted alkyl" means replacement of one or more alkyl hydrogens with aryl or halogen.

The term "optionally substituted alkylene chain" means replacement of an alkylene hydrogen with one or more alkyl groups, aryl groups or halogen atoms. Preferably, "optionally substituted alkylene chain" will mean replacement with one or more alkyl groups or halogen atoms, preferably alkyl groups.

The term "aryl" means a $C_{6-14}$ mono- or polycyclic aromatic ring system. Suitable carbocyclic aryl groups may be selected from, but are not limited to, phenyl, naphthyl, phenanthryl, anthracyl, indenyl, azulenyl, biphenyl, biphenylenyl and fluorenyl groups. Particularly preferred carbocyclic aryl groups are benzene and naphthalene.

The term "heteroaryl" means 3–7 membered monocyclic, or 7–14 membered polycyclic aromatic ring systems, independently containing one or more nitrogen, oxygen or sulfur atoms. Suitable heteroaryl groups may be selected from, but are not limited to, indole, pyridine, carbazole imidizole furan and the like. Preferred heteroaryl groups are pyridine, carbazol, furan and imidazole.

Non-aromatic heterocycles that are suitable for use in the present invention include, but are not limited to, pyrrolidine, piperidine and morpholine.

Exemplary preferred compounds that may be employed in this method of invention include, without limitation:

3-(2-piperidinylethyl)-2-(3-phenoxyphenyl)thiazolidin-4-one;

($\pm$)-3-(2-piperidinylethyl)-2-(2,2-diphenylethenyl)thiazolidin-4-one;

(+)-3-(2-piperidinylethyl)-2-(2,2-diphenylethenyl)thiazolidin-4-one;
(−)-3-(2-piperidinylethyl)-2-(2,2-diphenylethenyl)thiazolidin-4-one;
3-(2-piperidinylethyl)-2-(3-(4-tert-butylphenoxy)phenyl)thiazolidin-4-one;
3-(2-piperidinylethyl)-2-(2,2-diphenylethenyl)thiazinidin-4-one;
3-(2-piperidinylethyl)-2-(2-(4-chlorophenyl)furanyl)thiazolidin-4-one;
3-(2-piperidinylethyl)-2-(3-(3,4-dichlorophenoxy)phenyl)thiazolidin-4-one;
3-(2-piperidinylethyl)-2-(3-(3-trifluoromethylphenoxy)phenyl)thiazolidin-4-one;
3-(2-piperidinylethyl)-2-(3-benzyloxyphenyl)thiazolidin-4-one;
3-(2-piperidinylethyl)-2-(3-(4-chlorophenoxy)phenyl)thiazolidin-4-one;
3-(2-piperidinylethyl)-2-(3-(3,5-dichlorophenoxy)phenyl)thiazolidin-4-one;
3-(2-piperidinylethyl)-2-(4-(4-fluorophenoxy)phenyl)thiazolidin-4-one;
3-(2-piperidinylethyl)-2-(3-(4-methoxyphenoxy)phenyl)thiazolidin-4-one;
3-(2-piperidinylethyl)-2-(N-ethylcarbozolyl)thiazolidin-4-one;
3-(2-piperidinylethyl)-2-naphthylthiazolidin-4-one;
3-(2-piperidinylethyl)-2-(2,2-diphenylethenyl)thiazolidin-4-one;
3-(N,N-dimethylethylamino)-2-(2,2-diphenylethenyl)thiazolidin-4-one;
3-(N,N-dimethylethylamino)-2-(3-(4-tert-butyl)phenoxy)phenyl)thiazolidin-4-one;
3-(2-pyridinylmethyl)-2-(3-(4-tert-butyl)phenoxy)phenyl)thiazolidin-4-one;
3-(N,N-dimethylethylamino)-2-(2,2-diphenylethenyl)thiazinidin-4-one;
3-(N-benzyl-4-piperidinyl)-2-(3-phenoxyphenyl)thiazolidin-4-one;
3-(3-imidazolylpropyl)-2-(3-benzyloxypheny)thiazolidin-4-one;
3-(2-pyridinylmethyl)-2-(3-(3-trifluoromethylphenoxy)phenyl)thiazolidin-4-one;
3-(N,N-dimethylethylamino)-2-(3-(3,5-dichlorophenoxy)phenyl)thiazolidin-4-one;
3-(N,N-dimethylpropylamino)-2-(3-(3,5-dichlorophenoxy)phenyl)thiazolidin-4-one;
3-(N-benzyl-4-piperidinyl)-2-(4-(4-fluorophenoxy)phenyl)thiazolidin-4-one;
3-(2-pyrrolidinylethyl)-2-(3-(3,4-dichlorophenoxy)phenyl)thiazolidin-4-one;
3-(2-pyrrolidinylethyl)-2-(3-(3-trifluoromethylphenoxy)phenyl)thiazolidin-4-one;
3-(2-pyrrolidinylethyl)-2-(N-ethylcarbozole)thiazolidin-4-one;
3-(2-pyrrolidinylethyl)-2-(3-benzyloxyphenyl)thiazolidin-4-one;
3-(N-ethylmorpholinyl)-2-(3-(3,4-dichlorophenoxy)phenyl)thiazolidin-4-one;
3-(N,N-dimethylethylamino)-2-(3-(3,4-dichlorophenoxy)phenyl)thiazolidin-4-one;
3-(N,N-dimethylethylamino)-2-(3-(3-trifluoromethylphenoxy)phenyl)thiazolidin-4-one;
3-(3-imidazolylpropyl)-2-(3-(3-trifluoromethylphenoxy)phenyl)thiazolidin-4-one;
3-(N,N-dimethylpropylamino)-2-(3-(3-trifluoromethylphenoxy)phenyl)thiazolidin-4-one;
3-(N-ethylbenzylamino)-2-(3-(3-trifluoromethylphenoxy)phenyl)thiazolidin-4-one;
3-(N,N-diisopropylethylamino)-2-(3-(3-trifluoromethylphenoxy)phenyl)thiazolidin-4-one;
3-(N,N-dimethyl-2,2-dimethylpropylamino)-2-(3-(3,4-dichlorophenoxy)phenyl)thiazolidin-4-one;
3-(2-methylpiperidinyl-N-propyl)-2-(3-(3,4-dichlorophenoxy)phenyl)thiazolidin-4-one;
3-(N,N-dimethyl-2,2-dimethylpropylamino)-2-(3-(3-trifluoromethylphenoxy)phenyl)thiazolidin-4-one; and
3-(2-methylpiperidinyl-N-propyl)-2-(3-(3-trifluoromethylphenoxy)phenyl)thiazolidin-4-one;

as well as pharmaceutically acceptable salts thereof.

Particularly preferred compounds are selected from:
3-(2-piperidinylethyl)-2-(3-phenoxyphenyl)thiazolidin-4-one;
(±)-3-(2-piperidinylethyl)-2-(2,2-diphenylethenyl)thiazolidin-4-one;
(+)-3-(2-piperidinylethyl)-2-(2,2-diphenylethenyl)thiazolidin-4-one;
(−)-3-(2-piperidinylethyl)-2-(2,2-diphenylethenyl)thiazolidin-4-one;
3-(2-piperidinylethyl)-2-(3-(4-tert-butylphenoxy)phenyl)thiazolidin-4-one;
3-(2-piperidinylethyl)-2-(3-(3,4-dichlorophenoxy)phenyl)thiazolidin-4-one;
3-(2-piperidinylethyl)-2-(3-(3-trifluoromethylphenoxy)phenyl)thiazolidin-4-one;
3-(2-piperidinylethyl)-2-(3-benzyloxyphenyl)thiazolidin-4-one;
3-(2-piperidinylethyl)-2-(3-(4-chlorophenoxy)phenyl)thiazolidin-4-one;
3-(2-piperidinylethyl)-2-(3-(3,5-dichlorophenoxy)phenyl)thiazolidin-4-one;
3-(2-piperidinylethyl)-2-(4-(4-fluorophenoxy)phenyl)thiazolidin-4-one;
3-(N-benzyl-4-piperidinyl)-2-(3-phenoxyphenyl)thiazolidin-4-one;
3-(N-benzyl-4-piperidinyl)-2-(4-(4-fluorophenoxy)phenyl)thiazolidin-4-one;
3-(2-pyrrolidinylethyl)-2-(3-(3-trifluoromethylphenoxy)phenyl)thiazolidin-4-one;
3-(N-ethylbenzylamino)-2-(3-(3-trifluoromethylphenoxy)phenyl)thiazolidin-4-one;
3-(N,N-diisopropylethylamino)-2-(3-(3-trifluoromethylphenoxy)phenyl)thiazolidin-4-one;
3-(N,N-dimethyl-2,2-dimethylpropylamino)-2-(3-(3,4-dichlorophenoxy)phenyl)thiazolidin-4-one; and
3-(N,N-dimethyl-2,2-dimethylpropylamino)-2-(3-(3-trifluoromethylphenoxy)phenyl)thiazolidin-4-one;

as well as pharmaceutically acceptable salts thereof.

The invention disclosed herein is meant to encompass all pharmaceutically acceptable salts thereof of the disclosed compounds. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like.

The invention disclosed herein is also meant to encompass the in vivo metabolic products of the disclosed compounds. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein is also meant to encompass the disclosed compounds being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2H$, $^3H$, $^{13}C$ $^{14}C$, $^{15}N$, $^{18}O$, $^{17}O$, $^{31}P$, $^{32}P$, $^{35}S$, $^{18}F$, and $^{36}Cl$, respectively.

Some of the compounds disclosed herein may contain one or more asymmetric centers and may thus give rise to enantiomers, diastereomers, and other stereoisomeric forms. The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule. The phrase "enantiomeric excess" refers to a mixture wherein one enantiomer is present is a greater concentration than its mirror image molecule.

The invention is also directed to a method for treating disorders responsive to the blockade of sodium channels in mammals suffering thereof.

The thiazolidinone compounds of the invention may be used to treat humans or companion animals, such as dogs and cats. Particular preferred embodiments of the thiazolidinones of the invention for use in treating such disorders are represented as previously defined for Formula I.

The thiazolidinones of Formula I may be prepared using methods known to those skilled in the art. Specifically, the thiazolidones of the present invention were obtained by reacting one equivalent of an aldehyde and one equivalent of amine, with one equivalent of mercapto acid in toluene. The reaction was conducted at 85° C. for about 12 hours in the presence of 4-Angstrom molecular sieves. Scheme 1 shows the method of making the thiazolidinones of the invention, wherein $R_1$, $R_2$ and n are as previously defined.

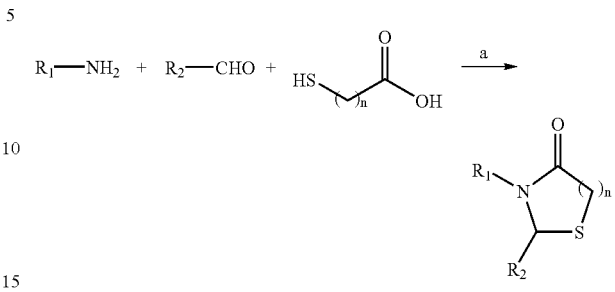

a) toluene, 4A molecular sieves, 85° C./12 h

The resulting compounds were purified by flash column chromatography.

The compounds of the present invention were assessed by electrophysiological assays in dissociated hippocampal neurons for sodium channel blocker activity. These compounds also could be assayed for binding to the neuronal voltage-dependent sodium channel using rat forebrain membranes and [$^3H$]BTX-B.

Sodium channels are large transmembrane proteins that are expressed in various tissues. They are voltage sensitive channels and are responsible for the rapid increase of $Na^+$ permeability in response to depolarization associated with the action potential in many excitable cells including muscle, nerve and cardiac cells.

One aspect of the present invention is the discovery of the mechanism of action of the compounds herein described as specific $Na^+$ channel blockers.

Based upon the discovery of this mechanism, these compounds are contemplated to be useful in treating or preventing neuronal loss due to focal or global ischemia, and in treating or preventing neurodegenerative disorders including ALS, anxiety, and epilepsy. They are also expected to be effective in treating, preventing or ameliorating neuropathic pain, surgical pain, chronic pain and tinnitus. The compounds are also expected to be useful as antiarrhythmics, anesthetics and antimanic depressants.

The present invention is directed to compounds of Formula I that are blockers of voltage-sensitive sodium channels. According to the present invention, those compounds having preferred sodium channel blocking properties exhibit an $IC_{50}$ of about 100 μM or less in the electrophysiological assay described herein. Preferably, the compounds of the present invention exhibit an $IC_{50}$ of 10 μM or less. Most preferably, the compounds of the present invention exhibit an $IC_{50}$ of about 1.0 μM or less. Compounds of the present invention may be tested for their Na+channel blocking activity by the following binding and electrophysiological assays.

In vitro Binding Assay:

The ability of compounds of the present invention to modulate either site 1 or site 2 of the $Na^+$ channel was determined following the procedures fully described in Yasushi, *J. Biol. Chem.* 261:6149–6152 (1986) and Creveling, *Mol. Pharmacol.* 23:350–358 (1983), respectively. Rat forebrain membranes are used as sources of $Na^+$ channel proteins. The binding assays are conducted in 130 μM choline chloride at 37° C. for 60-minute incubation with [$^3H$] saxitoxin and [$^3H$] batrachotoxin as radioligands for site 1 and site 2, respectively.

In vivo Pharmacology:

The compounds of the present invention may be tested for in vivo anticonvulsant activity after i.v., p.o. or i.p. injection using a number of anticonvulsant tests in mice, including the maximum electroshock seizure test (MES). Maximum electroshock seizures are induced in male NSA mice weighing between 15–20 g and male Sprague-Dawley rats weighing between 200–225 g by application of current (50 mA, 60 pulses/sec, 0.8 msec pulse width, 1 sec duration, D.C., mice; 99 mA, 125 pulses/sec, 0.8 msec pulse width, 2 sec duration, D.C., rats) using a Ugo Basile ECT device (Model 7801). Mice are restrained by gripping the loose skin on their dorsal surface and saline-coated corneal electrodes were held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results are treated in a quantal manner.

The compounds may be tested for their antinociceptive activity in the formalin model as described in Hunskaar, S., O. B. Fasmer, and K. Hole, *J. Neurosci. Methods* 14: 69–76 (1985). Male Swiss Webster NIH mice (20–30 g; Harlan, San Diego, Calif.) are used in all experiments. Food is withdrawn on the day of experiment. Mice are placed in Plexiglass jars for at least 1 hour to accommodate to the environment. Following the accommodation period mice are weighed and given either the compound of interest administered i.p. or p.o., or the appropriate volume of vehicle (10% Tween-80). Fifteen minutes after the i.p. dosing, and 30 minutes after the p.o. dosing mice are injected with formalin (20 μL of 5% formaldehyde solution in saline) into the dorsal surface of the right hind paw. Mice are transferred to the Plexiglass jars and monitored for the amount of time spent licking or biting the injected paw. Periods of licking and biting are recorded in 5 minute intervals for 1 hour after the formalin injection. All experiments are done in a blinded manner during the light cycle. The early phase of the formalin response is measured as licking/biting between 0–5 minutes, and the late phase is measured from 15–50 minutes. Differences between vehicle and drug treated groups are analyzed by one-way analysis of variance (ANOVA). A P value $\leq 0.05$ is considered significant. Activity in blocking the acute and second phase of formalin-induced paw-licking activity is indicative that compounds are considered to be efficacious for acute and chronic pain.

The compounds may be tested for their potential for the treatment of chronic pain (antiallodynic and antihyperalgesic activities) in the Chung model of peripheral neuropathy. Male Sprague-Dawley rats weighing between 200–225 g are anesthetized with halothane (1–3% in a mixture of 70% air and 30% oxygen) and their body temperature is controlled during anesthesia through use of a homeothermic blanket. A 2-cm dorsal midline incision is then made at the L5 and L6 level and the para-vertibral muscle groups retracted bilaterally. L5 and L6 spinal nerves are then be exposed, isolated, and tightly ligated with 6-0 silk suture. A sham operation is performed exposing the contralateral L5 and L6 spinal nerves as a negative control.

Tactile Allodynia: Rats are transferred to an elevated testing cage with a wire mesh floor and allowed to acclimate for five to ten minutes. A series of Semmes-Weinstein monofilaments are applied to the plantar surface of the hindpaw to determine the animal's withdrawal threshold. The first filament used possesses a buckling weight of 9.1 g (0.96 log value) and is applied up to five times to see if it elicited a withdrawal response. If the animal has a withdrawal response then the next lightest filament in the series is applied up to five times to determine if it can elicit a response. This procedure is repeated with subsequent less filaments until there is no response and the lightest filament that elicits a response is recorded. If the animal does not have a withdrawal response from the initial 9.1 g filament then subsequent filaments of increased weight are applied until a filament elicits a response and this filament is then recorded. For each animal, three measurements are made at every time point to produce an average withdrawal threshold determination. Tests are performed prior to and at 1, 2, 4 and 24 hours post drug administration. Tactile allodynia and mechanical hyperalgesia tests were conducted concurrently.

Mechanical Hyperalgesia: Rats are transferred to an elevated testing cage with a wire mesh floor and allowed to acclimate for five to ten minutes. A slightly blunted needle is touched to the plantar surface of the hindpaw causing a dimpling of the skin without penetrating the skin. Administration of the needle to control paws typically produces a quick flinching reaction, too short to be timed with a stopwatch and arbitrarily gives a withdrawal time of 0.5 second. The operated side paw of neuropathic animals exhibits an exaggerated withdrawal response to the blunted needle. A maximum withdrawal time of ten seconds is used as a cutoff time. Withdrawal times for both paws of the animals are measured three times at each time point with a five-minute recovery period between applications. The three measures are used to generate an average withdrawal time for each time point. Tactile allodynia and mechanical hyperalgesia tests are conducted concurrently.

The compounds may be tested for their neuroprotective activity after focal and global ischemia produced in rats or gerbils according to the procedures described in Buchan et al. (*Stroke*, Suppl. 148–152 (1993)) and Sheardown et al. (*Eur. J. Pharmacol.* 236:347–353 (1993)) and Graham et al. (*J. Pharmacol. Exp. Therap.* 276:1–4 (1996)).

The compounds may be tested for their neuroprotective activity after traumatic spinal cord injury according to the procedures described in Wrathall et al. (*Exp. Neurology* 137:119–126 (1996)) and Iwasaki et al. (*J. Neuro Sci.* 134:21–25 (1995)).

Electrophysiological Assay:

An electrophysiological assay was used to measure potencies of compounds of the present invention rBIIa/beta 1 sodium channels expressed in *Xenopus* oocytes.

Preparation of cRNA encoding cloned rat brain type IIa (rBIIa) and beta 1 (β1): cDNA clones encoding the rat brain beta 1 subunit are cloned in house using standard methods, and mRNA are prepared by standard methods. mRNA encoding rBIIa is provided by Dr. A. Golden (UC Irvine). The mRNAs are diluted and stored at −80° C. in 1 μL aliquots until injection.

Preparation of oocytes: Mature female *Xenopus laevis* are anaesthetized (20–40 min) using 0.15% 3-aminobenzoic acid ethyl ester (MS-222) following established procedures (Woodward, R. M., et al., *Mol. Pharmacol.* 41:89–103 (1992)).

Two to six ovarian lobes are surgically removed. Oocytes at developmental stages V–VI are dissected from the ovary, wherein the oocytes are still surrounded by enveloping ovarian tissues. Oocytes are defolliculated on the day of surgery by treatment with collagenase (0.5 mg/mL Sigma Type I, or Boehringer Mannheim Type A, for 0.5–1 hr). Treated oocytes are vortexed to dislodge epithelia, washed repeatedly and stored in Barth's medium containing 88 mM NaCl, 1 mM KCl, 0.41 mM CaCl$_2$, 0.33 mM Ca(NO$_3$)$_2$, 0.82 mM MgSO$_4$, 2.4 mM NaHCO$_3$, 5 mM HEPES, pH 7.4 adjusted with 0.1 mg/mL gentamycin sulphate.

Micro-injection of oocytes: Defolliculated oocytes are micro-injected using a Nanoject injection system (Drummond Scientific Co., Broomall, Pa.). Injection pipettes are beveled to minimize clogging. Tip diameter of injection pipettes is 15–35 µm. Oocytes are microinjected with approximately 50 nL 1:10 ratio mixtures of cRNAs for rBIIa and beta 1 respectively.

Electrophysiology: Membrane current responses are recorded in frog Ringer solution containing 115 mM NaCl, 2 mM KCl, 1.8 mM CaCl$_2$, 5 mM HEPES, pH 7.4. Electrical recordings are made using a conventional two-electrode voltage clamp (Dagan TEV-200) over periods ranging between 1–7 days following injection. The recording chamber is a simple gravity fed flow-through chamber (volume 100–500 mL depending on adjustment of aspirator). Oocytes are placed in the recording chamber, impaled with electrodes and continuously perfused (5–15 mL min$^{-1}$) with frog Ringer's solution. The tested compounds are applied by bath perfusion.

Voltage protocols for evoking sodium channel currents: The standard holding potential for whole oocyte clamp is –120 mV. Standard current-voltage relationships are elicited by 40 ms depolarizing steps starting from –60 mV to +50 mV in 10 mV increments. Peak currents are measured as the maximum negative current after depolarizing voltage steps. The voltage from maximum current response is noted and used for the next voltage protocol.

The purpose is to find compounds that are state dependent modifiers of neuronal sodium channels. Preferably, the compounds have a low affinity for the rested/closed state of the channel, but a high affinity for the inactivated state. The following voltage protocol is used to measure a compounds affinity for the inactivated state. Oocytes are held at a holding potential of –120 mV. At this membrane voltage, nearly all of the channels are in the closed state. Then a 4 second depolarization is made to the voltage where the maximum current is elicited. At the end of this depolarization, nearly all the channels are in the inactivated state. A 10 ms hyperpolarizing step is then made in order to remove some channels from the inactivated state. A final depolarizing test pulse is used to assay the sodium current after this prolonged depolarization (see analysis below). Sodium currents are measured at this test pulse before and after the application of the tested compound. Data is acquired using pCLAMP 8.0 software and analyzed with CLAMPFIT software (Axon instruments).

Data analysis: Apparent inhibition constants ($K_i$ values) for antagonists are determined from single point inhibition data using the following equation (a generalized form of the Cheng-Prusoff equation) (Leff, P. and I. G. Dougall, TiPS 14:110–112 (1993)).

$$K_i = (FR/1-FR)*[drug] \qquad \text{Eq.2}$$

Where FR is the fractional response and is defined as sodium current elicited from the final depolarizing test pulse prior to application of the drug divided by the sodium current measured in the presence of the drug. [drug] is the concentration of the drug used.

Drugs: Drugs are initially made up at concentrations of 2–10 mM in DMSO. Dilutions are then made to generate a series of DMSO stocks over the range 0.3 µM to 10 mM—depending upon the potency of the compound. Working solutions are made by 1000–3000 fold dilution of stocks into Ringer.

At these dilutions DMSO alone has little or no measurable effects on membrane current responses. DMSO stocks of drugs are stored in the dark at 4° C. Ringer solutions of drugs are made up fresh each day of use.

Compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for epilepsy, neurodegenerative diseases, anesthetic, arrhythmia, manic depression, and chronic pain. For intramuscular injection, the dose is generally about one-half of the oral dose.

In the method of treatment or prevention of neuronal loss in global and focal ischemia, brain and spinal cord trauma, hypoxia, hypoglycemia, status epilepsy and surgery, the compound can be administrated by intravenous injection at a dose of about 0.025 to about 10 mg/kg.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular thiazolidinones of the present invention, with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts are formed by mixing a solution of the thiazolidinone compound of the present invention with a solution of a pharmaceutically acceptable non-toxic base such as sodium hydroxide, potassium hydroxide, choline hydroxide, sodium carbonate and the like.

The pharmaceutical compositions of the invention may be administered to any animal that may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner that is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings that, if desired, are resistant to gastric juices. For this purpose, concentrated saccharide solutions may be used, which may optionally contain gum arabic, talc, polyvinyl pyrrolidone, poly-ethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which can be used rectally, include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension, and include, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

The Ki values for compounds of the present invention are provided in Table 1 below.

Inhibition Constants (Ki) for Preferred
Thiazolidin-4-one Compounds

| Ki (oocyte) NM | $R_1$ | $R_2$ | n |
|---|---|---|---|
| 430 | propyl-piperidine | 3-methylphenyl phenyl ether | 1 |

-continued
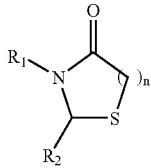
| Ki (oocyte) NM | R₁ | R₂ | n |
|---|---|---|---|
| 290 | 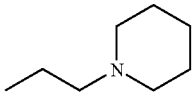 | 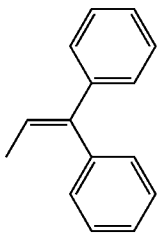 | 1 |
| 180 | 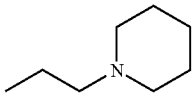 | 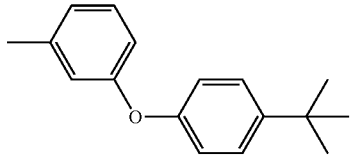 | 1 |
| 3580 | 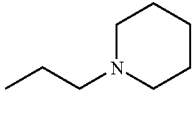 | 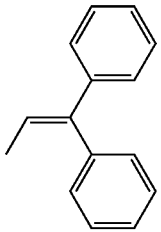 | 2 |
| 600 | 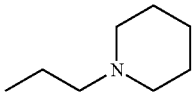 | 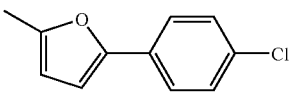 | 1 |
| 180 | 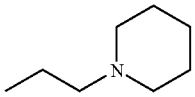 | 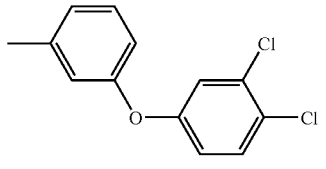 | 1 |
| 90 | 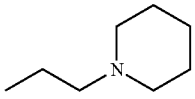 | 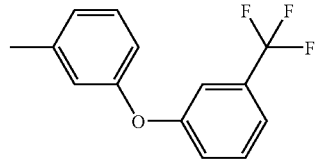 | 1 |
| 390 | 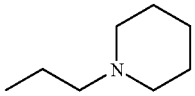 | 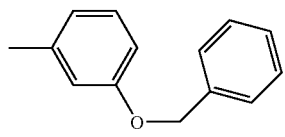 | 1 |

-continued
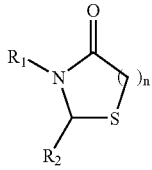
| Ki (oocyte) NM | R₁ | R₂ | n |
|---|---|---|---|
| 390 | 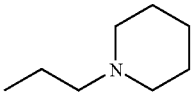 | 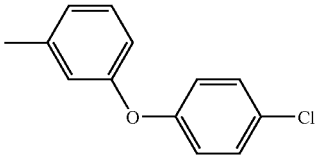 | 1 |
| 130 | 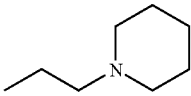 | 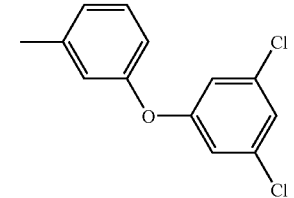 | 1 |
| 500 | 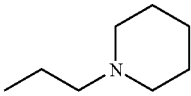 | 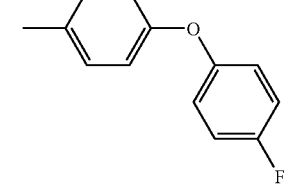 | 1 |
| 800 | 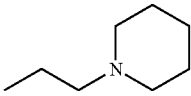 | 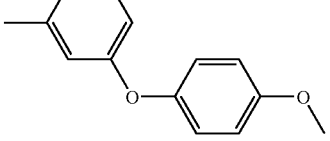 | 1 |
| 1120 | 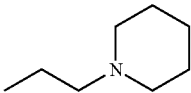 | 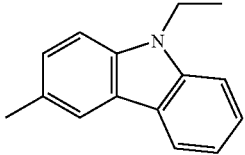 | 1 |
| 330 | 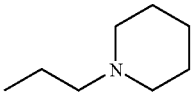 | 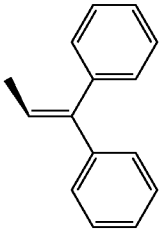 | 1 |

-continued

Structure: thiazolidinone ring with R₁ on N, R₂ on C2, (CH₂)ₙ, C=O at C4

| Ki (oocyte) NM | R₁ | R₂ | n |
|---|---|---|---|
| 760 | propyl-piperidine | 1,1-diphenyl-propen-1-yl (methyl substituted) | 1 |
| 11930 | propyl-piperidine | phenyl | 1 |
| 5350 | propyl-piperidine | phenylethynyl | 1 |
| 8790 | propyl-piperidine | styryl (cinnamyl) | 1 |
| 27310 | propyl-piperidine | propyl | 1 |
| 18690 | propyl-piperidine | butyl | 1 |
| 2830 | propyl-piperidine | 1-naphthyl | 1 |
| 70690 | propyl-piperidine | —CH₃ | 1 |
| 3480 | propyl-pyrrolidine | 1,1-diphenyl-propen-1-yl | 1 |

-continued
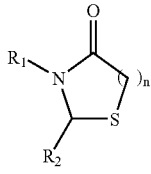
| Ki (oocyte) NM | R₁ | R₂ | n |
|---|---|---|---|
| 2600 | 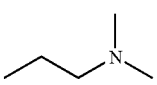 | 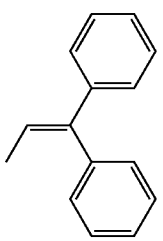 | 1 |
| 840 | 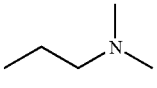 | 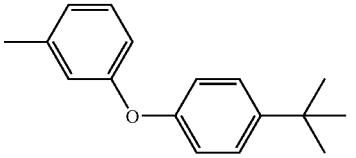 | 1 |
| 1220 | 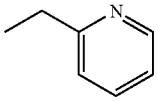 | 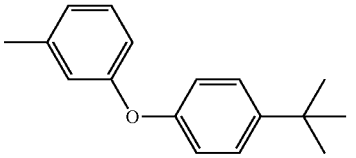 | 1 |
| 20030 | 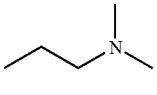 | 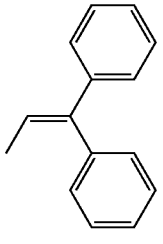 | 2 |
| 250 | 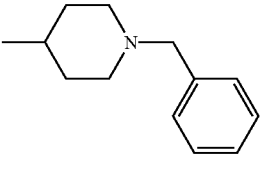 | 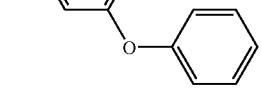 | 1 |
| 6550 |  | 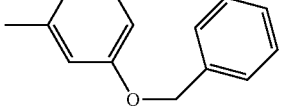 | 1 |
| 3400 | 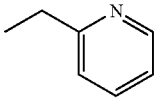 | 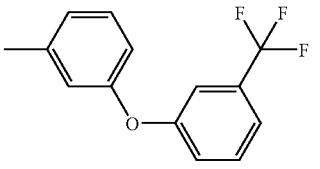 | 1 |

-continued

| Ki (oocyte) NM | R₁ | R₂ | n |
|---|---|---|---|
| 840 | propyl-N(CH₃)₂ | 3-methylphenyl-O-(3,5-dichlorophenyl) | 1 |
| 1880 | butyl-N(CH₃)₂ | 3-methylphenyl-O-(3,5-dichlorophenyl) | 1 |
| 280 | (4-methylpiperidin-1-yl)benzyl | 4-methylphenyl-O-(4-fluorophenyl) | 1 |
| 900 | propyl-pyrrolidinyl | 3-methylphenyl-O-(3,4-dichlorophenyl) | 1 |
| 420 | propyl-pyrrolidinyl | 3-methylphenyl-O-(3-trifluoromethylphenyl) | 1 |
| 7400 | propyl-pyrrolidinyl | 9-ethyl-3-methylcarbazolyl | 1 |
| 3430 | propyl-pyrrolidinyl | 3-methylphenyl-O-benzyl | 1 |

-continued
| Ki (oocyte) NM | R₁ | R₂ | n |
|---|---|---|---|
| 810 | 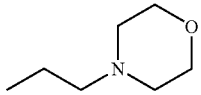 | 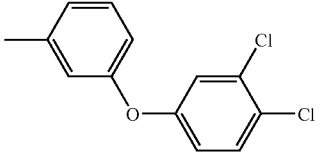 | 1 |
| 720 | 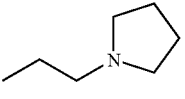 | 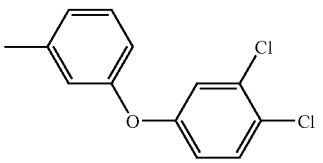 | 1 |
| 710 | 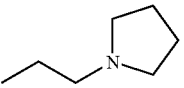 | 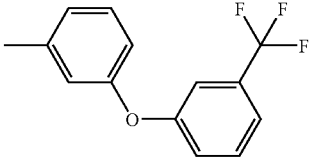 | 1 |
| 1150 | 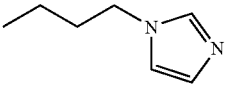 | 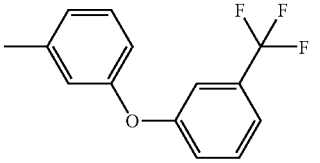 | 1 |
| 2750 | 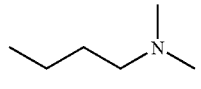 | 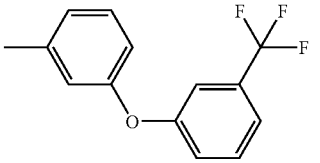 | 1 |
| 50 | 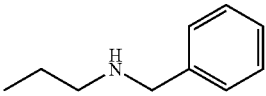 | 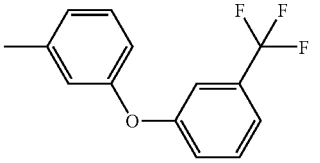 | 1 |
| 30 | 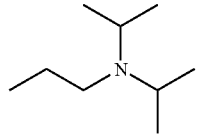 | 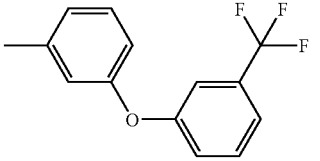 | 1 |

-continued

| Ki (oocyte) NM | $R_1$ | $R_2$ | n |
|---|---|---|---|
| 390 | neopentyl-N(CH3)2 | 3-(3,4-dichlorophenoxy)phenyl | 1 |
| 880 | 2-methylpiperidinyl-butyl | 3-(3,4-dichlorophenoxy)phenyl | 1 |
| 230 | neopentyl-N(CH3)2 | 3-(3-trifluoromethylphenoxy)phenyl | 1 |
| 1320 | 2-methylpiperidinyl-butyl | 3-(3-trifluoromethylphenoxy)phenyl | 1 |

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

The invention claimed is:

1. A compound having the Formula I:

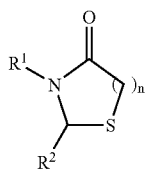

or a pharmaceutically acceptable salt, or solvate thereof, wherein:

n is 1;

$R_1$ is selected from the group consisting of:

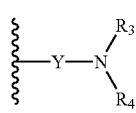

where Y is alkylene, and $R_3$ and $R_4$ are the same or different and are selected from hydrogen, alkyl, aryl, or arylalkyl, or $R_3$ and $R_4$ together form an alkylene chain having 4 to 5 carbon atoms optionally interrupted by a nitrogen or oxygen;

(ii) pyridylalkyl; and (iii) piperidin-4-yl, optionally substituted by alkyl, aryl or aralkyl; and $R_2$ is selected from the group consisting of:

(i) optionally substituted phenoxyphenyl;

(ii) optionally substituted phenylthiophenyl;

(iii) optionally substituted benzyloxyphenyl;

(iv) optionally substituted benzylthiophenyl;

(v)

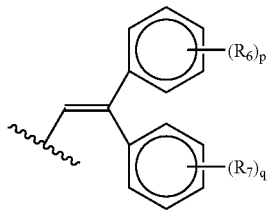

wherein R₆ and R₇ are independently hydrogen or alkyl; and p and q are integers from 0 to 4;

(vi)

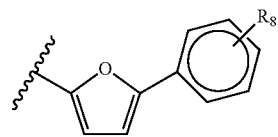

wherein R₈ is hydrogen, halogen or alkyl;

(vii)

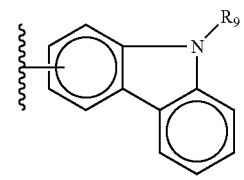

wherein R₉ is hydrogen or alkyl; and
(viii) naphthalenyl.

2. The compound according to claim 1, wherein R₁ is

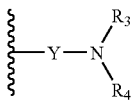

and Y is ethylene or propylene.

3. The compound according to claim 1, wherein R₁ is (i)

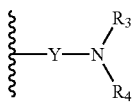

where R₃ and R₄ together form an alkylene chain having 4 to 5 carbon atoms;
Y is a C₁₋₆ alkylene chain; and
R₂ is phenoxyphenyl or benzyloxyphenyl, wherein the phenoxy moiety is optionally substituted with alkyl, halogen or haloalkyl.

4. The compound according to claim 3, wherein R₃ and R₄ together form an alkylene chain of 5 carbon atoms; and Y is a C₂₋₄ alkylene chain.

5. The compound according to claim 3, wherein R₃ and R₄ together form an alkylene chain of 4 carbon atoms, and Y is a C₂₋₄ alkylene chain.

6. The compound according to claim 1, wherein R₁ is

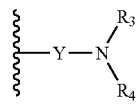

where R₃ and R₄ are independently hydrogen, alkyl or arylalkyl, Y is a C₁₋₄ alkylene chain; and
R₂ is phenoxyphenyl or benzyloxyphenyl, wherein the phenoxy moiety is optionally substituted with alkyl, halogen or haloalkyl.

7. The compound according to claim 1, wherein R₁ is pyridyl(C₁₋₄)alkyl.

8. The compound according to claim 7, wherein R₂ is phenoxyphenyl or benzyloxyphenyl, wherein the phenoxy moiety is optionally substituted with alkyl, halogen or haloalkyl.

9. The compound of claim 8, wherein R₁ is pyridylmethyl, pyridylethyl or pyridylpropyl.

10. The compound according to claim 1, wherein R₁ is an optionally substituted piperidin-4-yl.

11. The compound according to claim 10, wherein R₁ is 1-benzylpiperidin-4-yl.

12. The compound according to claim 1, wherein R₂ is

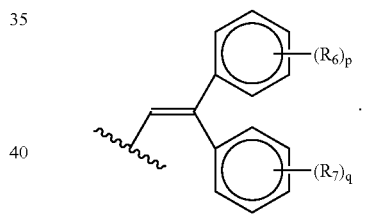

13. The compound according to claim 12, wherein R₁ is

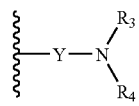

where R₃ and R₄ together form an alkylene chain having 4 to 5 carbon atoms;
Y is a C₁₋₆ alkylene chain.

14. The compound according to claim 12, wherein R₁ is

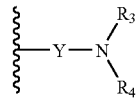

where R₃ and R₄ are independently hydrogen, alkyl or arylalkyl, and Y is a C₁₋₆ alkylene chain.

15. The compound of claims 13 or 14, wherein p=0.

16. The compound according to claim 1, wherein $R_2$ is

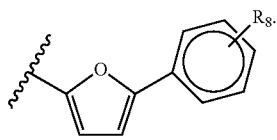

17. The compounds according to claim 16, wherein $R_1$ is

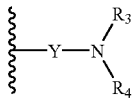

where $R_3$ and $R_4$ together form an alkylene chain having 4 to 5 carbon atoms;
Y is a $C_{1-6}$ alkylene chain.

18. The compound according to claim 16, wherein $R_1$ is

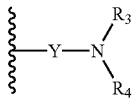

where $R_3$ and $R_4$ are independently hydrogen, alkyl or arylalkyl, and Y is a $C_{1-6}$ alkylene chain.

19. The compound according to claim 16, wherein $R_8$ is hydrogen.

20. The compound according to claim 1, wherein $R_2$ is

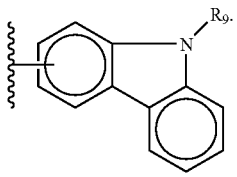

21. The compound according to claim 20, wherein $R_1$ is

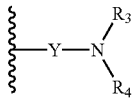

where $R_3$ and $R_4$ together form an alkylene chain having 4 to 5 carbon atoms;
Y is a $C_{1-6}$ alkylene chain.

22. The compound according to claim 20, wherein $R_1$ is

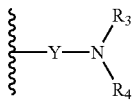

where $R_3$ and $R_4$ are independently hydrogen, alkyl or arylalkyl, and Y is a $C_{1-6}$ alkylene chain.

23. The compound according to claim 1, wherein $R_2$ is naphthalenyl.

24. The compound according to claim 23, wherein $R_1$ is

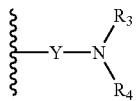

where $R_3$ and $R_4$ together form an alkylene chain having 4 to 5 carbon atoms;
Y is a $C_{1-6}$ alkylene chain.

25. The compound according to claim 23, wherein $R_1$ is

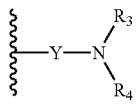

where $R_3$ and $R_4$ are independently hydrogen, alkyl or arylalkyl, and Y is a $C_{1-6}$ alkylene chain.

26. The compound according to claim 1, wherein said compound is selected from the group consisting of:
- 3-(2-piperidinylethyl)-2-(3-phenoxyphenyl)thiazolidin-4-one;
- (±)-3-(2-piperidinylethyl)-2-(2,2-diphenylethenyl)thiazolidin-4-one;
- (+)-3-(2-piperidinylethyl)-2-(2,2-diphenylethenyl)thiazolidin-4-one;
- (−)-3-(2-piperidinylethyl)-2-(2,2-diphenylethenyl)thiazolidin-4-one;
- 3-(2-piperidinylethyl)-2-(3-(4-tert-butylphenoxy)phenyl)thiazolidin-4-one;
- 3-(2-piperidinylethyl)-2-(2-(4-clorophenyl)furanyl)thiazolidin-4-one;
- 3-(2-piperidinylethyl)-2-(3-(3,4-dichlorophenoxy)phenyl)thiazolidin-4-one;
- 3-(2-piperidinylethyl)-2-(3-(3-trifluoromethylphenoxy)phenyl)thiazolidin-4-one;
- 3-(2-piperidinylethyl)-2-(3-benzyloxyphenyl)thiazolidin-4-one;
- 3-(2-piperidinylethyl)-2-(3-(4-chlorophenoxy)phenyl)thiazolidin-4-one;
- 3-(2-piperidinylethyl)-2-(3-(3,5-dichlorophenoxy)phenyl)thiazolidin-4-one;
- 3-(2-piperidinylethyl)-2-(4-(4-fluorophenoxy)phenyl)thiazolidin-4-one;
- 3-(2-piperidinylethyl)-2-(3-(4-methoxyphenoxy)phenyl)thiazolidin-4-one;
- 3-(2-piperidinylethyl)-2-(N-ethylcarbozolyl)thiazolidin-4-one;
- 3-(2-piperidinylethyl)-2-naphthyl thiazolidin-4-one;
- 3-(2-piperidinylethyl)-2-(2,2-diphenylethenyl)thiazolidin-4-one;
- 3-(N,N-dimethylethylamino)-2-(2,2-diphenylethenyl)thiazolidin-4-one;
- 3-(N,N-dimethylethylamino)-2-(3-(4-tert-butyl)phenoxy)phenyl)thiazolidin-4-one;
- 3-(2-pyridinylmethyl)-2-(3-(4-tert-butyl)phenoxy)phenyl)thiazolidin-4-one;
- 3-(N-benzyl-4-piperidinyl)-2-(3-phenoxyphenyl)thiazolidin-4-one;
- 3-(3-imidazolylpropyl)-2-(3-benzyloxyphenyl)thiazolidin-4-one;

3-(2-pyridinylmethyl)-2-(3-(3-trifluoromethylphenoxy)phenyl)thiazolidin-4-one;
3-(N,N-dimethylethylamino)-2-(3-(3,5-dichlorophenoxy)phenyl)thiazolidin-4-one;
3-(N,N-dimethylpropylamino)-2-(3-(3,5-dichlorophenoxy)phenyl)thiazolidin-4-one;
3-(N-benzyl-4-piperidinyl)-2-(4-(4-fluorophenoxy)phenyl)thiazolidin-4-one;
3-(2-pyrrolidinylethyl)-2-(3-(3,4-dichlorophenoxy)phenyl)thiazolidin-4-one;
3-(2-pyrrolidinylethyl)-2-(3-(3-trifluoromethylphenoxy)phenyl)thiazolidin-4-one;
3-(2-pyrrolidinylethyl)-2-(N-ethylcarbozole)thiazolidin-4-one;
3-(2-pyrrolidinylethyl)-2-(3-benzyloxyphenyl)thiazolidin-4-one;
3-(N-ethylmorpholinyl)-2-(3-(3,4-dichlorophenoxy)phenyl)thiazolidin-4-one;
3-(N,N-dimethylethylamino)-2-(3-(3,4-dichlorophenoxy)phenyl)thiazolidin-4-one;
3-(N,N-dimethylethylamino)-2-(3-(3-trifluoromethylphenoxy)phenyl)thiazolidin-4-one;
3-(3-imidazolylpropyl)-2-(3-(3-trifluoromethylphenoxy)phenyl)thiazolidin-4-one;
3-(N,N-dimethylpropylamino)-2-(3-(3-trifluoromethylphenoxy)phenyl)thiazolidin-4-one;
3-(N-ethylbenzylamino)-2-(3-(3-trifluoromethylphenoxy)phenyl)thiazolidin-4-one;
3-(N,N-diisopropylethylamino)-2-(3-(3-trifluoromethylphenoxy)phenyl)thiazolidin-4-one;
3-(N,N-dimethyl-2,2-dimethylpropylamino)-2-(3-(3,4-dichlorophenoxy)phenyl)thiazolidin-4-one;
3-(2-methylpiperidinyl-N-propyl)-2-(3-(3,4-dichlorophenoxy)phenyl)thiazolidin-4-one;
3-(N,N-dimethyl-2,2-dimethylpropylamino)-2-(3-(3-trifluoromethylphenoxy)phenyl)thiazolidin-4-one; and
3-(2-methylpiperidinyl-N-propyl)-2-(3-(3-trifluoromethylphenoxy)phenyl)thiazolidin-4-one.

27. A pharmaceutical composition, comprising the compound of claim 1, and a pharmaceutically acceptable carrier or diluent.

28. A method of making a compound according to claim 1 wherein said method comprises reacting:
(i) an amine having the Formula II:

   $R_1$—$NH_2$   II and
(ii) an aldehyde having the Formula III:

   $R_2$—CHO   III in the presence of a mercapto acid having the Formula IV:

IV

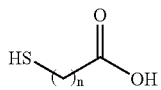

wherein $R_1$, $R_2$ and n are as defined in claim 1.

29. The method according to claim 28, wherein the reaction is conducted in the presence of toluene.

30. The method according to claim 28, wherein the reaction is conducted in the presence of at least one 4 Angstrom molecular sieve.

31. The method according to claim 28, wherein the reaction is conducted at a temperature of from about 50° C. to about 110° C.

32. The method according to claim 28, wherein the reaction is conducted for about 2 hours to about 24 hours.

33. A method of treating or ameliorating a disorder responsive to blockage of sodium channels in a mammal suffering therefrom, comprising administering to a mammal in need of such treatment an effective amount of a compound according to claim 1, or a pharmaceutically acceptable salt thereof, wherein said disorder is selected from the group consisting of: neuronal damage, acute or chronic pain, depression, diabetic neuropathy, and amyotrophic lateral sclerosis (ALS).

34. The method according to claim 33, wherein said neuronal damage is caused by focal or global ischemia.

35. The method according to claim 33, wherein said disorder is amyotrophic lateral sclerosis (ALS).

36. The method according to claim 33 wherein said mammal is a human, dog or cat.

37. A pharmaceutical composition for treatment of a mammal having a disorder or condition responsive to blockage of sodium channels, which comprises an amount of the compound according to claim 1, or a pharmaceutically effective salt thereof, that is effective for treating said disorder or condition, and a pharmaceutically acceptable carrier wherein said disorder or condition is selected from the group consisting of: neuronal damage, acute or chronic pain, depression, diabetic neuropathy, and amyotrophic lateral sclerosis.

38. The compound according to claim 26, wherein said compound is selected from the group consisting of:
3-(2-piperidinylethyl)-2-(3-phenoxyphenyl)thiazolidin-4-one;
(±)-3-(2-piperidinylethyl)-2-(2,2-diphenylethenyl)thiazolidin-4-one;
(+)-3-(2-piperidinylethyl)-2-(2,2-diphenylethenyl)thiazolidin-4-one;
(−)-3-(2-piperidinylethyl)-2-(2,2-diphenylethenyl)thiazolidin-4-one;
3-(2-piperidinylethyl)-2-(3-(4-tert-butylphenoxy)phenyl)thiazolidin-4-one;
3-(2-piperidinylethyl)-2-(3-(3,4-dichlorophenoxy)phenyl)thiazolidin-4-one;
3-(2-piperidinylethyl)-2-(3-(3-trifluoromethylphenoxy)phenyl)thiazolidin-4-one;
3-(2-piperidinylethyl)-2-(3-benzyloxyphenyl)thiazolidin-4-one;
3-(2-piperidinylethyl)-2-(3-(4-chlorophenoxy)phenyl)thiazolidin-4-one;
3-(2-piperidinylethyl)-2-(3-(3,5-dichlorophenoxy)phenyl)thiazolidin-4-one;
3-(2-piperidinylethyl)-2-(4-(4-fluorophenoxy)phenyl)thiazolidin-4-one;
3-(N-benzyl-4-piperidinyl)-2-(3-phenoxyphenyl)thiazolidin-4-one;
3-(N-benzyl-4-piperidinyl)-2-(4-(4-fluorophenoxy)phenyl)thiazolidin-4-one;
3-(2-pyrrolidinylethyl)-2-(3-(3-trifluoromethylphenoxy)phenyl)thiazolidin-4-one;
3-(N-ethylbenzylamino)-2-(3-(3-trifluoromethylphenoxy)phenyl)thiazolidin-4-one;
3-(N,N-diisopropylethylamino)-2-(3-(3-trifluoromethylphenoxy)phenyl)thiazolidin-4-one;

3-(N,N-dimethyl-2,2-dimethylpropylamino)-2-(3-(3,4-dichlorophenoxy)phenyl)thiazolidin-4-one; and
3-(N,N-dimethyl-2,2-dimethylpropylamino)-2-(3-(3-trifluoromethylphenoxy)phenyl)thiazolidin-4-one.

39. A compound selected from the group consisting of:
3-(2-piperidinylethyl)-2-phenylthiazolidin-4-one;
3-(2-piperidinylethyl)-2-(2-phenylethynyl)thiazolidin-4-one;
3-(2-piperidinylethyl)-2-(2-phenylethenyl)thiazolidin-4-one;
3-(2-piperidinylethyl)-2-ethylthiazolidin-4-one;
3-(2-piperidinylethyl)-2-propylthiazolidin-4-one; and
3-(2-piperidinylethyl)-2-methylthiazolidin-4-one.

* * * * *